United States Patent [19]
Kelton et al.

[11] Patent Number: 5,744,448
[45] Date of Patent: Apr. 28, 1998

[54] HUMAN FOLLICLE STIMULATING HORMONE RECEPTOR

[75] Inventors: Christie Ann Kelton, Hopkinton; Shirley Vui Yen Cheng, Boston; Noreen Patrice Nugent, Framingham; Rene Lynn Schweickhardt, Quincy, all of Mass.

[73] Assignee: Applied Research Systems ARS Holding N.V., Curacao, Netherlands Antilles

[21] Appl. No.: 487,886

[22] Filed: Jun. 7, 1995

Related U.S. Application Data

[62] Division of Ser. No. 670,085, Mar. 15, 1991.
[51] Int. Cl.$^6$ .................. A61K 38/16; C07K 14/72
[52] U.S. Cl. ............... 514/12; 424/158.1; 514/841; 514/843; 530/350
[58] Field of Search ............ 424/158.1, 192.1; 514/2, 8, 12, 841, 843; 435/69.1; 530/350, 397, 398, 850

[56] References Cited

U.S. PATENT DOCUMENTS

| | | | |
|---|---|---|---|
| 4,652,450 | 3/1987 | Sluss et al. | 424/115 |
| 4,921,808 | 5/1990 | Schneyer et al. | 436/503 |

FOREIGN PATENT DOCUMENTS 9013643  11/1990  WIPO .

OTHER PUBLICATIONS

Sprengel, R., et al., *Mol. Endocrinol.*, vol. 4, 525 (1990).
Parmentier, M., et al., *Science*, vol. 246, 1620 (1989).
Minegish, T., et al., *Biochem. Biophys. Res. Comm.*, vol. 175, 1125 (29 Mar. 1991).
Reichart, L., Jr., et al., "Biochemical Studies on FSH and Its Receptor", *Glycoprotein Hormones*, W. Chin and I. Boime, eds., (Serono Symposia USA, 1990).

*Primary Examiner*—Stephen Walsh
*Assistant Examiner*—Lorraine M. Spector
*Attorney, Agent, or Firm*—Browdy and Neimark

[57] ABSTRACT

The present invention embraces essentially pure human FSH receptor, or a fragment or mutant thereof which binds FSH, DNA encoding said receptor, fragment or mutant, expression vectors comprising said DNA, cells transfected with said expression vectors, and methods of producing said receptor, fragment or mutant by culturing said transfected cells. The present invention also includes pharmaceutical compositions comprising said receptor, fragment or mutant, as well as methods of treating patients with such compositions to reduce endogenous FSH bioactivity. An improved assay for human FSH using the receptor, fragment or mutant of the present invention is also disclosed.

15 Claims, 3 Drawing Sheets

HUMAN FOLLICLE STIMULATING HORMONE RECEPTOR

CROSS-REFERENCE TO RELATED APPLICATIONS

The present application is a divisional of U.S. application Ser. No. 07/670,085, filed Mar. 15, 1991.

BACKGROUND OF THE INVENTION

This invention relates to human follicle stimulating hormone receptor and its synthesis by recombinant DNA techniques.

Follicle stimulating hormone (FSH) is a pituitary-derived heterodimeric glycoprotein hormone which shares structural similarities with luteinizing hormone (LH) and thyroid stimulating hormone (TSH), both of which are also produced in the pituitary gland, and chorionic gonadotropin (CG), which is produced in the placenta. The hormones are relatively large (28–38 kilodaltons) and are composed of a common α subunit non-covalently bound to a distinct β subunit that confers receptor binding specificity.

The cellular receptors for these hormones are known to be members of the G protein-coupled class of membrane-bound receptors which when activated stimulate an increase in the activity of adenylyl cyclase. This results in an increase in the level of the intracellular second messenger adenosine 3',5'-monophosphate (cAMP), which in turn causes increased steroid synthesis and secretion. Hydropathicity plots of the amino acid sequences of these receptors reveal three general domains: (1) a hydrophilic amino-terminal region, considered to be the amino-terminal extracellular domain, (2) seven hydrophobic segments of membrane-spanning length, considered to be the transmembrane domain, and (3) a carboxy-terminal region which contains potential phosphorylation sites (serine, threonine, and tyrosine residues), considered to be the carboxy-terminal intracellular or cytoplasmic domain. The glycoprotein hormone receptor family is distinguished from other G protein-coupled receptors, such as the β2-adrenergic, rhodopsin, and substance K receptors, by the large size of the hydrophilic amino-terminal domain, which is involved in hormone binding.

The FSH receptor is expressed on testicular Sertoli cells and ovarian granulosa cells. While there has been a recognized need for providing essentially pure human FSH receptor, purification of naturally derived preparations is not practical and would not likely be sufficient to permit determination of the amino acid sequence. Recently, one group has cloned the cDNA encoding the rat FSH receptor, deduced the amino acid sequence, and expressed it in mammalian cells (Sprengel, Mol. Endocrinol. 4:525, 1990). Another group, attempting to clone the TSH receptor, apparently also cloned and identified a portion of the transmembrane region of the human FSH receptor (Parmentier, Science 246:1620, 1989).

SUMMARY OF THE INVENTION

The present invention embraces essentially pure human FSH receptor, or a fragment or mutant thereof which binds FSH, DNA encoding said receptor, fragment or mutant, expression vectors comprising said DNA, cells transfected with said expression vectors, and methods of producing said receptor, fragment or mutant by culturing said transfected cells. The present invention also includes pharmaceutical compositions comprising said receptor, fragment or mutant, as well as methods of treating patients with such compositions to reduce endogenous FSH bioactivity. An improved assay for human FSH using the receptor, fragment or mutant of the present invention is also disclosed.

DETAILED DESCRIPTION OF THE INVENTION

Figure 1:
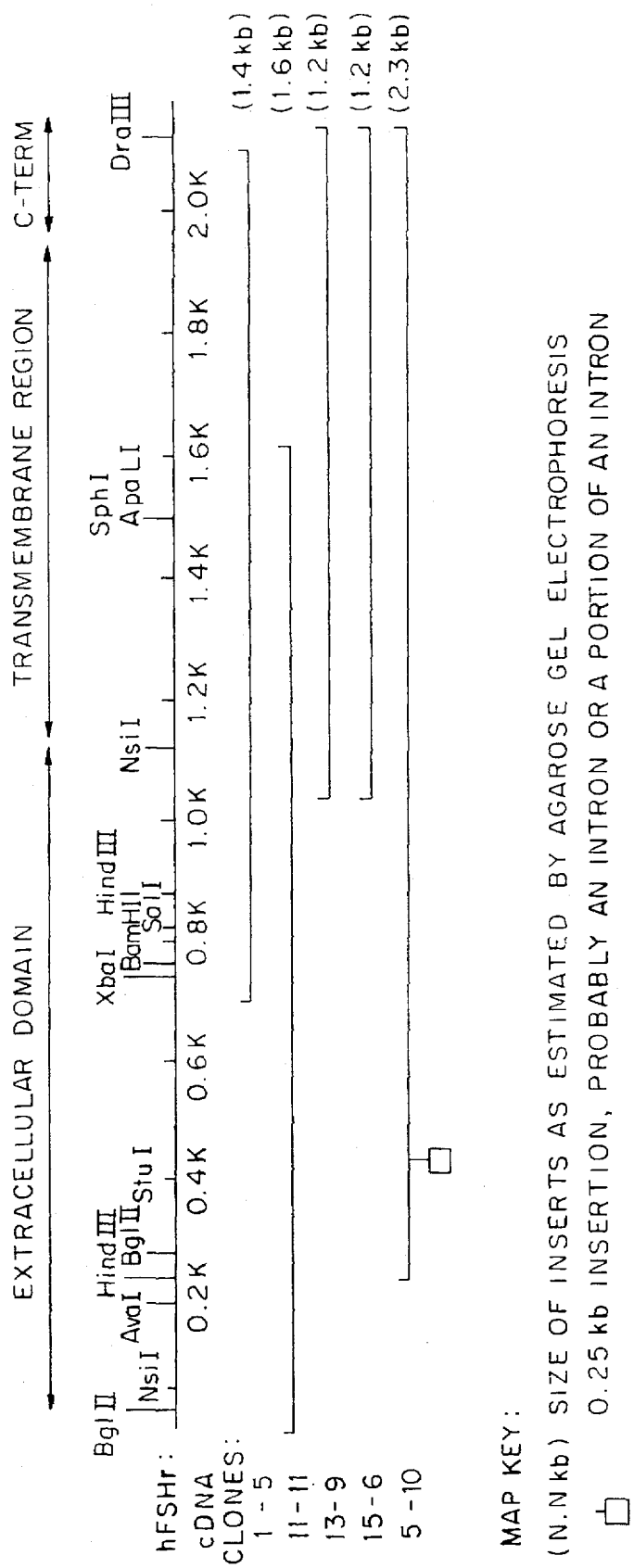
FIG. 1 is a map of the human FSH receptor cDNA clones. A partial restriction endonuclease map is shown which was determined by combining DNA sequence data derived from portions of each of the five clones. Size increments of 0.2 kilobase pair (K) are marked. The regions to which the clones correspond are indicated by the solid lines below the restriction endonuclease map. The clone designation and the approximate size in kilobase pairs are indicated to the left and right of each solid line, respectively. Approximate locations of the amino-terminal extracellular domain, transmembrane domain, and carboxy-terminal intracellular domain of the encoded protein are indicated by the dashed arrows above the restriction endonuclease map. The position of an insertion (probably an intron or a portion of an intron) in the 5–10 clone is indicated by the open box.

As used herein, human FSH receptor, and its FSH-binding fragments or mutants, refers to polypeptides which are capable of recognizing and selectively binding with human FSH and which produce no significant immunological response in humans. Thus, the present invention includes human FSH receptor having the amino acid sequence depicted in Sequence ID No:2, as well as FSH-binding fragments or mutants thereof which retain a very high degree of homology (i.e. at least 95% identity) with the depicted amino acid sequence, or with at least the extracellular portion thereof. Fragments of the human FSH receptor embraced by the present invention include those fragments remaining after the cytoplasmic and/or the transmembrane domains have been deleted from the full polypeptide. An especially preferred fragment embraced by the present invention is the amino-terminal extracellular portion comprising approximately amino acids 1 to 349 of the human FSH receptor amino acid sequence shown in Sequence ID No:2. Since some of the loops which span the transmembrane regions (listed in features section, Sequence ID No:2) are also extracellular, these may be linked (e.g. through appropriate spacer molecules) to a fragment containing the amino-terminal extracellular portion to improve binding. The polypeptide may be glycosylated, as in the natural receptor, or may be partially or completely deglycosylated.

It is further contemplated that only a portion of the above-described amino-terminal extracellular domain may be effectively utilized to bind FSH since it is very likely that the complete extracellular domain is not necessary for this purpose. Thus, a fragment which is somewhat shorter than the 349 amino acids of the complete extracellular domain may be readily produced and tested for effective binding to FSH. So long as the FSH-binding region of the extracellular portion is maintained intact, the length of the overall fragment utilized is not critical. For this reason, it is also expected that non-interfering amino acids can be added to either end of the extracellular domain, or FSH-binding fragment thereof, without adversely affecting the FSH-binding capacity of the polypeptide. Accordingly, this invention embraces a fragment of the human FSH receptor which comprises a substantial portion of the extracellular domain and which retains substantially the same FSH-binding characteristics as the complete extracellular domain.

Mutant forms of the above-described receptor and fragments are also within the scope of the present invention. Such mutants include conservative substitutions in one to ten amino acid residues, the location and nature of such substitutions being selected so as not to significantly degrade the FSH-binding characteristics of the receptor or fragment thereof which is modified.

Essentially pure human FSH receptor is prepared by isolating and cloning the DNA encoding it from a cDNA or genomic library, ligating the DNA into a vector, transfecting host cells with the vector, culturing transfected host cells under conditions which permit expression of the receptor, fragment or mutant, and recovering the receptor, fragment or mutant from the culture.

The DNA which is used to make expression vectors may be genomic DNA or cDNA encoding human FSH receptor, and may contain regions which enhance expression, such as introns, promoters, enhancers, etc. The DNA may be readily modified by substitution, deletion or insertion of nucleotides (e.g. by site-specific mutagenesis) that do not adversely affect the biological or FSH-binding activity of the expressed protein. For example, conservative substitutions (mutations) which alter from one to ten amino acids may be made without adversely affecting the overall structure and activity of the expressed protein (mutein). Likewise, certain portions of the DNA, such as those portions which code for the cytoplasmic and/or transmembrane domains, may be deleted so that only a fragment, such as the soluble extracellular domain, of the protein is expressed. The human FSH receptor or FSH-binding fragment or mutant thereof may also be expressed as a fusion protein. One such fusion protein would include a polypeptide at the carboxy-terminus which would confer characteristics which would facilitate purification of the protein, or immobilization of the purified protein on a solid substrate for use in FSH assays or FSH purification protocols. Another such fusion protein would include a cleavable polypeptide at the amino-terminus which would facilitate expression.

Human FSH receptor produced in accordance with the present invention is essentially pure, meaning that it is substantially free of biological adventitious agents normally associated with FSH receptor extracted from natural sources, such as, for example, bacteria, viruses, and other proteins. The receptor may be formulated into pharmaceutical compositions by mixing with suitable pharmaceutically acceptable carriers in a manner known to those skilled in the art.

Generally, pharmaceutical compositions may be formulated for oral, parenteral (including subcutaneous, intramuscular, and intravenous), vaginal, rectal, buccal (including sublingual), transdermal or intranasal administration. Compositions for parenteral administration are normally in the form of a liquid solution, dispersion, or emulsion, preferably isotonic; for vaginal or rectal administration, as a cream or suppository; for oral or buccal administration, as a tablet or capsule; and for intranasal administration, as a powder, nasal drop or aerosol. Various slow release, depot implant or injectable dosage forms may be utilized. The active component may also be incorporated into polymer matrices, liposomes and microspheres to control delivery.

These compositions may conveniently be administered in unit dosage form and may be prepared by any of the methods well-known in the pharmaceutical art. Formulations for parenteral administration may contain as common excipients sterile water or saline, alkylene glycols such as propylene glycol, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Formulations for nasal administration may be in powder form and contain as excipients, for example, lactose or dextran, or may be aqueous or oily solutions for administration in the form of nasal drops or metered spray. For buccal administration, typical excipients include sugars, calcium stearate, pregelatinated starch and the like. One or more surfactant acids or salts can be added to the solution or powder formulation. Suitable pharmaceutically acceptable surfactant salts will be those which retain the phenomenon of enhanced peptide absorption, as well as the compound's surfactant characteristics and which are not deleterious to the subject or otherwise contraindicated.

The dosage of active ingredient administered, as well as the route and frequency of administration, will obviously depend upon the needs and condition of the patient being treated, the therapeutic effect which is sought, and the judgement of the doctor conducting the treatment.

Pharmaceutical compositions comprising human FSH receptor, or FSH-binding fragments or mutants thereof, may be administered to a patient in therapeutically effective doses to bind with endogenous circulating FSH in the patient and thereby control the available level of bioactive FSH. Thus, pharmaceutical compositions of the present invention are effectively utilized to reduce endogenous FSH bioactivity. In a female patient, such treatment may be effectively used to prevent follicle growth and maturation, thereby preventing pregnancy. In a male patient, such treatment may be effectively used to prevent spermatogenesis. A particularly suitable pharmaceutical composition for the above purpose comprises a fragment of the human FSH receptor which comprises the amino-terminal extracellular domain or a substantial portion thereof with substantially the same FSH-binding characteristics.

Essentially pure human FSH receptor may also be advantageously utilized in conventional receptor assays for FSH, such as, for example, that disclosed in Reichert, Endocrinolgy 94:483, 1974. Substitution of the pure receptor of the present invention will substantially improve the consistency and performance of such assays. The receptor can also be incorporated into a stable cell line, particularly a mammalian cell line, capable of producing a measurable biological response upon stimulation of the receptor. Measurement of cell response in the presence of FSH under assay (e.g. in test serum, plasma, culture media, tissue homogenates, etc.) would provide an indication of bioactivity, and thereby provide a highly useful diagnostic assay. Such a cell line could also be used to screen chemical libraries for substances that may interact with the FSH receptor or to test peptides or small proteins for their ability to bind to the FSH receptor in a rapid through-put screening system. An example of a rapid through-put screening system may be one in which the binding of a ligand to the recombinant FSH receptor results in the generation of cAMP which activates the luciferase gene operatively linked to a cAMP response element and can be quantitated by the measurement of bioluminescence. A fragment comprising the amino-terminal extracellular domain or an FSH-binding fragment and/or fusion protein thereof can be linked to an affinity column to purify FSH from fluids, extracts, etc.

Essentially pure human FSH receptor or FSH-binding fragments or mutants thereof can also be used in X-ray crystallographic analysis to develop molecular models. Such models are useful in defining the tertiary structure of the hormone-binding domains of the human FSH receptor. Such information would provide insight into the structure of the actual regions of contact between FSH and its receptor, thus aiding the design of peptides which have FSH agonistic or antagonistic activity.

The recombinant techniques suitable for producing the proteins and DNA of the present invention, including identification of suitable mutation techniques, vectors, host cells, culture conditions, etc., are well-known to those skilled in the art and are adequately described, for example, in U.S. Pat. No. 4,761,371 and WO 88/09818, the disclosures of which are incorporated herein by reference. The experimental protocols, bacterial and bacteriophage culture media and chemical solutions used in the examples below are described in detail in Sambrook, "Molecular Cloning: A Laboratory Manual," 2nd ed., Cold Spring Harbor Laboratory Press, 1989, unless otherwise referenced.

EXAMPLE 1

Isolation and Characterization of Human FSH Receptor cDNA Clones

Library Screening.

A rat FSH receptor CDNA clone similar to that described by Sprengel, Mol. Endocrinol. 4:525, 1990 was obtained from Dr. William Moyle, University of Medicine and Dentistry of New Jersey-Robert Wood Johnson Medical School. This cDNA clone was inserted into the SV40 late expression vector pSVL (Pharmacia LKB, product number 27-4509-01) and was designated pSVLFSHR. A 2.1 kilobase pair (kb) DNA fragment containing the region corresponding to the complete rat FSH receptor protein coding region was excised from the plasmid using the restriction endonuclease sites XbaI and BamHI. The digested DNA was size-fractionated by gel electrophoresis, and the 2.1 kb rat FSH receptor fragment was purified by electroelution from the gel. This purified DNA fragment was used as a probe for library screening to identify human FSH receptor cDNA clones.

A lambda gt11 CDNA library, constructed from RNA extracted from human testis, was purchased from Clontech, Palo Alto, Calif. A (catalogue number HL1010b) and was amplified prior to use. Twenty aliquots of the amplified library, equivalent to approximately $7.5 \times 10^4$ plaque forming units (pfu), were each adsorbed to about 0.5 milliliters (ml) of a plating suspension of E. coli strain Y1088. The suspension had been prepared by growing an overnight culture of Y1088 at 37° C. in NZYM or LB supplemented with 0.2% maltose and 10 millimolar (mM) $MgSO_4$, pelleting the cells, and then resuspending them in 10 mM $MgSO_4$ to an $O.D._{600}$ of 0.5. About 6.5 ml of molten NZYM top agarose (0.7%), at a temperature of 48° C., was added to each phage/cell suspension and the resulting mixture was poured onto one of twenty 150 millimeter (mm) NZYM agar plates (prewarmed to 42° C.). The total number of phage plated for the primary screen was about $1.5 \times 10^6$. After a 4 hour incubation at 42° C., followed by chilling at 4° C. for several hours, duplicate nitrocellulose filter (Millipore) plaque lifts were generated from each plate according to the procedures of Benton and Davies (Science, 196:180, 1977). The random oligonucleotide priming procedure of Feinberg and Vogelstein (Anal. Biochem. 137:266, 1983) was used to generate, from the template rat FSH receptor DNA fragment described in the preceding paragraph, a $^{32}P$-labeled probe of a specific activity of $1-2 \times 10^9$ counts per minute (cpm)/microgram (µg). Prehybridization of the nitrocellulose filter phage lifts was done in a buffer containing 50% formamide, 5×SSC [1×SSC is 0.15 molar (M) sodium chloride, 0.015M sodium citrate], 20 mM sodium phosphate buffer, pH 7.2, 10×Denhardt's reagent (50×Denhardt's reagent is 1% Ficoll, 1% polyvinylpyrrolidone and 1% bovine serum albumin) and 100 µg/ml tRNA at 37° C. for about 6 hours. Hybridization of the filters was done in the same buffer except that the rat FSH receptor DNA probe was added at a concentration of about $3 \times 10^6$ cpm/ml buffer. After hybridization for 16–24 hours at 37° C., excess probe was washed from the filters in 2×SSC, 0.1% SDS at room temperature for 30 minutes, then 0.2× SSC, 0.1% SDS at 37° C. for 60 minutes. The filters were subsequently exposed to XAR film (Kodak) overnight at −70° C. Six duplicate positives were identified from the primary library screen. With the wide end of a pasteur pipette, plaque-containing agar plugs were removed from the 150-mm plates in the regions in which the positive clones were located. The phage were eluted by soaking the plugs in SM. The suspended phage were then replated onto 150-mm NZYM agar plates as described for the primary screen. Plates which contained about 500 plaque forming units per plate were selected for secondary screening. The procedures used for filter lifts and filter hybridizations for the secondary screen were the same as described for the primary screen.

Following the secondary screen, 5 putative human FSH receptor positives were identified and isolated as purified λgt11 bacteriophage clones. They were assigned the following designations: 1-5, 5-10, 11-11, 13-9, and 15-6.

Determination of the DNA Sequences of the Putative Human FSH Receptor cDNA Clones.

Bacteriophage DNA was prepared from each of the λgt11 cDNA isolates using the plate lysate method described in Sambrook, "Molecular Cloning: A Laboratory Manual," 2nd ed., Cold Spring Harbor Laboratory Press, 1989, page 2.118. The bacteriophage DNA was digested with EcoRI restriction endonuclease, and then size-fractionated in an agarose gel for purification of the cDNA insert fragments. The purified CDNA inserts were subcloned into the EcoRI site of pUC18 in order to facilitate subsequent cloning and sequencing manipulations. Double-stranded plasmid DNA was purified from 5 ml cultures of the host strain E. coli MC1061 by the small-scale alkaline lysis method (Sambrook, ibid. p. 1.25), then further purified by passage over Elutip-d columns (Schleicher & Schuell, Keene, NH) using the manufacturer's protocol. Half of the plasmid DNA obtained from each small-scale plasmid preparation was then denatured in 0.2 normal (N) NaOH, 0.2 mM EDTA in a volume of 20 microliters (µl) at room temperature for 10 minutes. The denatured plasmid DNA was neutralized and ethanol precipitated by adding 7.5 µl of 7.5M ammonium acetate and 110 µl 100% ethanol and chilling the mixture in liquid nitrogen. The DNA precipitate was pelleted by centrifugation in a microfuge for 10 minutes. The DNA pellets were washed in 70% ethanol and dried. Sequencing reactions were done with Sequenase T7 DNA polymerase (United States Biochemical) according to the manufacturer's specifications. Preliminary sequencing reactions were done with forward and reverse sequencing primers (Pharmacia LKB) for the pUC18 polylinker region. Data generated from preliminary sequencing was used to design human FSH receptor-specific sequencing primers. The primers were either synthesized on a model 391 Applied Biosystems DNA synthesizer or ordered from National Biosciences, Inc., Hamel, Minn. Some DNA sequence data was obtained by subcloning smaller restriction endonuclease fragments of the original clones into pUC18 and repeating sequencing reactions with the forward and reverse primers.

Preliminary sequence data showed that none of the five cDNA isolates represented the full-length protein coding region of the human FSH receptor, but that the combined sequence data from the clones could be used to infer the complete protein sequence. A schematic diagram of the relative locations of each of the five clones in relation to a map of the complete human FSH receptor cDNA sequence is shown in FIG. 1. The complete human ISH receptor cDNA sequence, obtained by combining the sequence readings from the overlapping clones using the Genetics Computer Group (GCG) fragment assembly computer program, is depicted in Sequence ID No:1 and the inferred amino acid sequence is depicted in Sequence ID No:2. Analysis of the human FSH receptor DNA sequence resulted in the identification of a long open reading frame of 2085 nucleotides which encoded a protein of 695 amino acids. The human FSH receptor is thereforlonger than the acids longer than the rat FSH receptor. The overall percent identities between the rat and human FSH receptor DNA and protein sequences were determined using the GCG Bestfit program and were 86% and 89%, respectively. The extracellular amino-terminal hydrophilic portion of the human FSH receptor is estimated to be 349 amino acids in length, and shares 87% identity with the corresponding region of the rat FSH receptor. The seven membrane spanning regions of the two species, which are bridged by three extracellular and three intracellular loops, share 95% identity, and the carboxyterminal intracellular regions share only 81% identity. The partial amino acid sequence published by Parmentier, Science 246:1620–1622, 1989, corresponds to amino acids 399 to 525 in Sequence ID No:2.

Clone 5-10 was a variant in that it contained an insertion of 0.25 kb after the T at nucleotide position 448 in Sequence ID No:1. The DNA sequence of the insertion was not similar to any portion of the rat or human FSH receptor DNA sequence and also was not similar to any known sequence in the Genbank or EMBL DNA sequence databases. The corresponding region in clone 11—11 did not contain this insertion. LH receptor cDNA clones isolated from a human thyroid cDNA library contain similar variations (Frazier, Mol. Endocrinol. 4:1264–1276, 1990). These variants are likely derived from incompletely and/or aberrantly spliced mRNA molecules. The presence of a 3' splice consensus sequence (CAG'G) at the 3' junction of the 5-10 insertion is evidence which supports this explanation.

The pUC18 plasmids harboring the 11—11 (called pHFSHR11—11), 15-6 (called pHFSHR15-6), and 5-10 (called pHFSHR5-10) cDNA inserts were deposited in the American Type Culture Collection (ATCC), Rockville, MD, on Mar. 1, 1991 and have received the accession numbers ATCC68538, ATCC68540, and ATCC68539, respectively. These deposits were made in accordance with all of the requirements of the Budapest Treaty.

EXAMPLE 2

Expression of Human FSH Receptor in Mammalian Cells and Demonstration of Bioactivity
Construction of Vectors for the Expression of the Full-Length Human FSH Receptor in Mammalian Cells.

Figure 2:
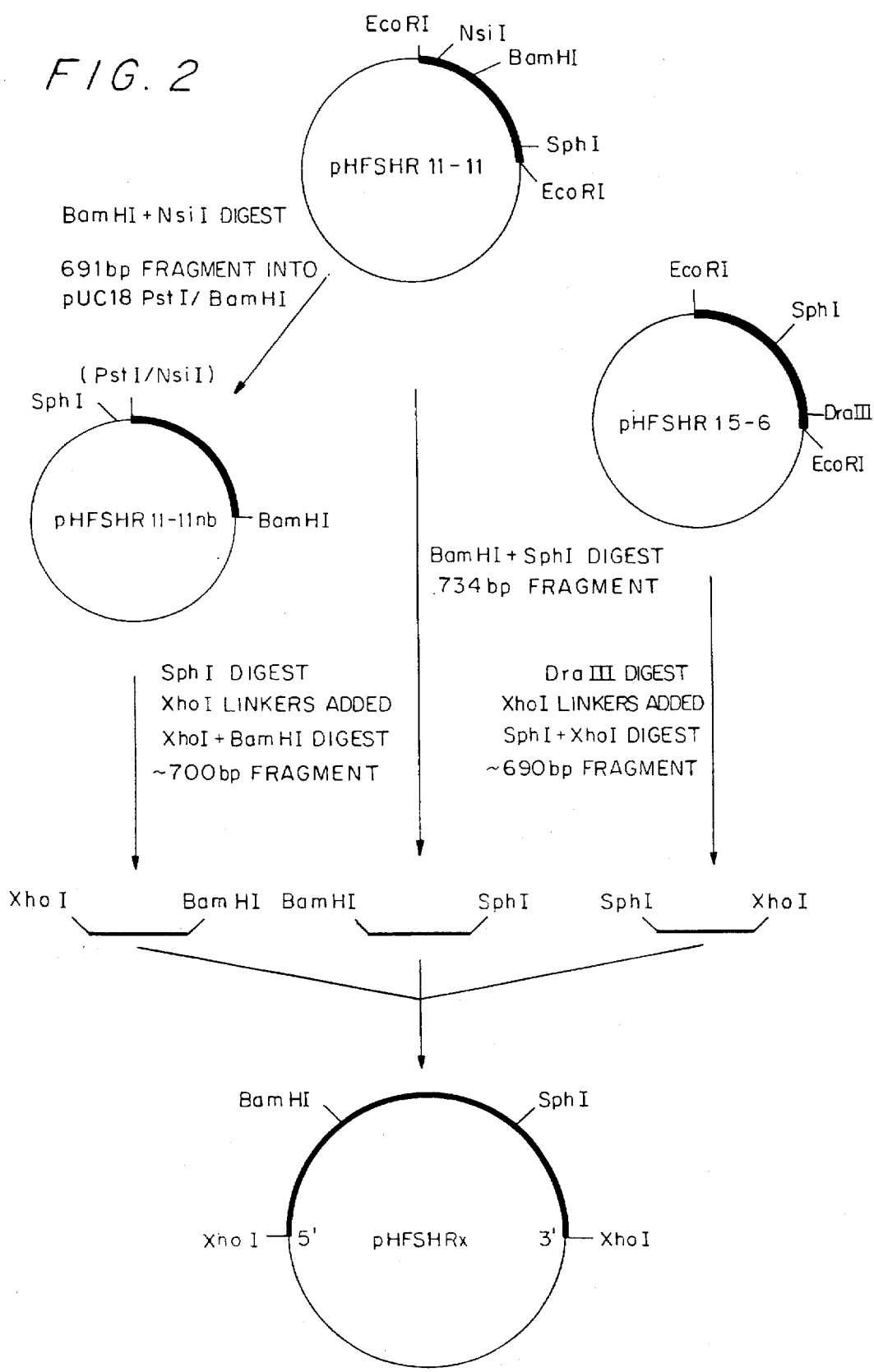
FIG. 2 is a strategy for engineering a human FSH receptor DNA construction for the purpose of expression of the protein in a mammalian cell line.
Figure 3:
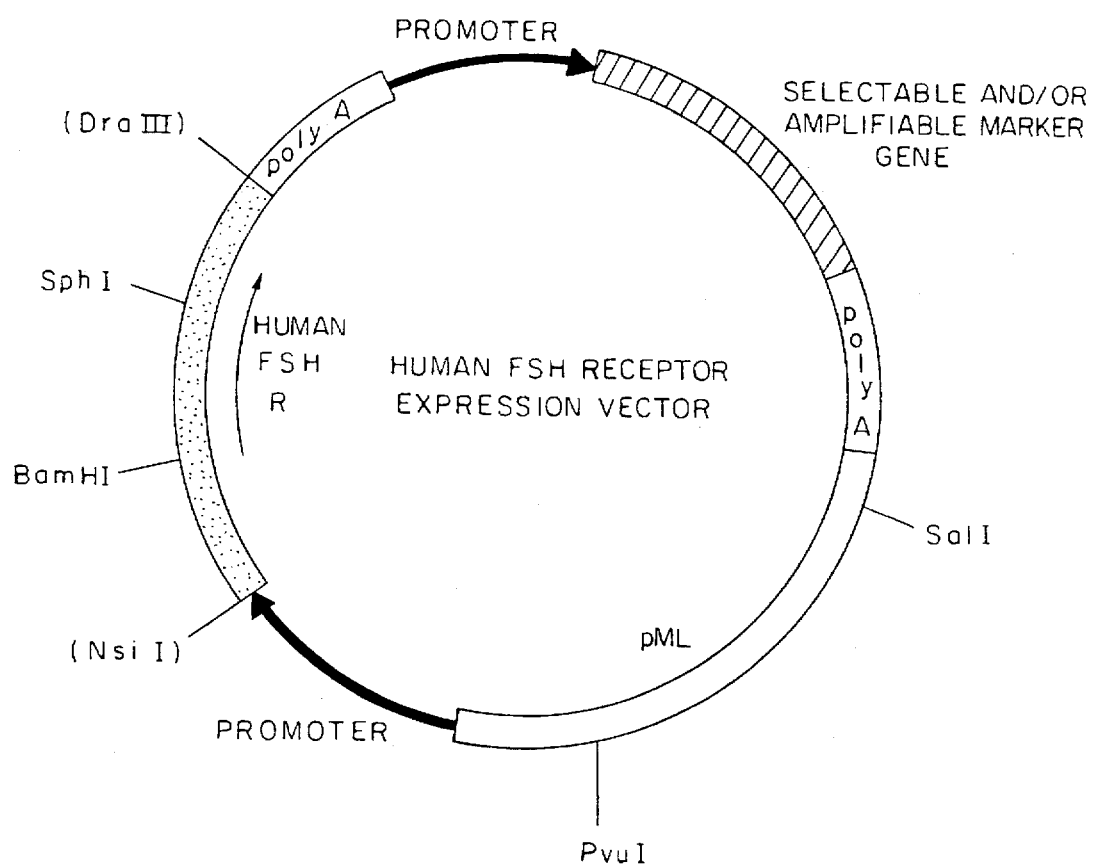
FIG. 3 is a map of a plasmid vector useful for the expression of the human FSH receptor in mammalian cells.

The strategy for the engineering a human FSH receptor DNA construct for expression in mammalian cells is shown in FIG. 2. The 5' 691 base pair (bp) NsiI-BamHI fragment which contains the start ATG is purified from pHFSHR11-11 and subcloned into pUC18 digested with PstI and BamHI. The resulting plasmid, pHFSHR11-11nb, is linearized with SphI. The termini are blunted by treatment with T4 polymerase or the Klenow fragment of DNA polymerase I (New England Biolabs, Beverly, Mass.). After ligation of XhoI linkers (New England Biolabs, Beverly, Mass.) to the blunted termini, the mixture is digested with XhoI and BamHI and the approximately 700 bp human FSH receptor 5' fragment is gel purified. A fragment from the middle region of the human FSH receptor CDNA is isolated from pHFSHR11-11 by digestion with BamHI and SphI and gel purification of the appropriate 734 bp piece. The 3' human FSH receptor fragment, which contains the TAA stop codon, is isolated from pHFSHR15-6 by first digesting the plasmid with DraIII, then blunting the termini in a reaction with T4 DNA polymerase or the Klenow fragment of E. coli DNA polymerase I. XhoI linkers are ligated to the blunted ends and the resulting mixture is digested with SphI and XhoI and then size-fractionated so that the 3' 690 bp (approximately) SphI-XhoI fragment is isolated and purified. The complete human FSH receptor expression construction is assembled, with the 5' XhoI-BamHI, middle BamHI-SphI, and 3' SphI-XhoI human FSH receptor fragments, as a 2.1 kb XhoI fragment in pUC-XhoI (created in this laboratory by converting the SmaI site in the pUC18 polylinker to an XhoI site with XhoI linkers). Correct assembly of the construction is verified by restriction endonuclease digestion and DNA sequencing. The human FSH receptor expression construction is then purified as a 2.1 kb XhoI fragment and inserted into the XhoI site of an expression vector so that a plasmid such as the one depicted in FIG. 3 is obtained. If the expression vector selected does not have a suitable XhoI cloning site, linkers can be used to convert either the fragment termini or the vector cloning site into compatible sites. Transcription of the human FSH receptor coding region and the marker gene (for selection and/or amplification) is initiated by a eukaryotic promoter such as the mouse metallothoinein I (MMT-I), Rous Sarcoma Virus (RSV) or simian virus 40 early or late (SV40E, SV40L) promoters. Suitable marker genes are the neomycin resistance gene (Neo), the dihydrofolate reductase (DHFR) gene, and the multidrug resistance gene (MDR). A polyadenylation signal (poly A), usually the SV40 early polyadenylation region, is also provided for the processing of the receptor gene and the marker gene transcripts. The expression vector also includes pML, a derivative of pBR322 which contains the ampicillin resistance gene and a bacterial origin of replication, to enable growth and propagation of the plasmid in a suitable E. coli strain.

Similarly, DNA cloning and engineering techniques can be used by those skilled in the art to modify the human FSH receptor DNA expression construction so that FSH-binding fragments are encoded. These modified DNA fragments can be inserted into an expression vector similar to the one shown in FIG. 3 and used to transfect mammalian cells to develop lines which secrete soluble FSH-binding fragments of the human FSH receptor.

Demonstration of Bioactivity by Transient Transfection of COS-7 Cells with the Human FSH Receptor-Containing Expression Vector.

To test the hormone mediated activation of the recombinant human FSH receptor, the human FSH receptor expression vector construct is transfected into COS-7 cells which are stimulated with FSH to elicit a biological response measured by an increase in the amount of intracellular cAMP levels.

The vector plasmid DNA is purified by two sequential high-speed centrifugations through cesium chloride density gradients. Exponentially growing COS-7 cells (ATCC CRL 1651) are transfected with the DNA using a modification of the DEAE-dextran transfection protocol of Seed and Aruffo (PNAS 84:3366, 1987). COS-7 cells are seeded in growth medium in six well plates at a density of $1 \times 10^5$ cells per well. Growth medium for COS-7 cells is Dulbecco's modified Eagle's medium (DMEM) supplemented with 10% fetal bovine serum (FBS) and 1% L-glutamine. After 16 to 25 hours incubation at 37° C., the medium is removed and the cells washed twice with phosphate-buffered saline (PBS). A DNA mixture containing the human FSH expression vector plasmid, or a control vector plasmid which does not include the human FSH receptor cDNA insert, is added dropwise to the center of the culture in each well. The dishes are swirled gently to distribute the mixtures evenly. The DNA mixture for each well is prepared by the following method: (1) 2 µg vector plasmid DNA is diluted in PBS so that the total volume is 136 µl, (2) 68 µl of a solution of 2 mg/ml DEAE-dextran (Pharmacia LKB), 0.9% NaCl is diluted in 68 µl PBS, and (3) the solutions made in (1) and (2) are combined to obtain a DNA mixture in a total volume of 272 µl. Mock-transfected control cells are treated with the same solution expect that DNA is omitted. After a 15 minute incubation at 37° C., the DNA or mock mixture is gently removed and the cells are washed twice with PBS. Growth medium which also contains 100 micromolar (µM) chloroquine diphosphate (Sigma) is added and the cells are left to incubate at 37° C. for 3 hours. The medium is removed, the cells are washed with DMEM and then incubated at 37° C. for 48 hours in growth medium.

Each well of cells is subsequently washed with 3 ml of growth medium and then pre-incubated in 700 µl of DMEM (without FBS) containing 0.1 mM 3-isobutyl-1-methylxanthine (Sigma) for 15 minutes at 37° C. Following pre-incubation, purified human FSH or LH is added to the medium in each well and incubation is continued for an additional 30 min at 37° C. The assay is then terminated by four cycles of rapid freezing and thawing. 50 µl of cell lysate is removed for protein determination. To the remaining lysate, which is to be processed for cAMP determination, 840 µl of ice cold ethanol is added. Both aliquots are centrifuged at 13,000×g for 15 minutes to remove cell debris. Determination of the total protein content in each 50 µl aliquot of cell lysate sample is carried out using the Bio-Rad Protein Assay kit (catalogue No. 500-0002).

cAMP assays are done using the RIANEN cAMP ($^{125}$I) RIA kit, catalogue number NEK-033, purchased from Dupont/NEN Medical Products, Boston, Mass. The solutions used in the following protocol are provided in the kit. 200 µl of the hormonally stimulated or non-stimulated cell lysate is dried-down and resuspended in cAMP assay buffer. The samples are acetylated and brought to a final volume of 1 ml. 100 µl of samples and a set of acetylated cAMP standards are added to 100 µl of tracer cAMP solution followed by the addition of 100 µl antiserum complex. The mixtures are incubated at 4° C. for overnight. The mixtures are precipitated with 500 µl of precipitator solution, centrifuged at 1200×g for 15 minutes. The supernatant is removed and the activity remaining in the pellets is measured in a Packard Cobra auto gamma counter.

If a suitable range of FSH concentrations is used for stimulation of the human FSH receptor-expressing cells, such as, for example, 0.01 to 1000 nanograms per milliliter, a cAMP dose response curve can be generated which shows a proportional increase in cAMP levels as increased amounts of FSH are used for cell stimulation.

EXAMPLE 3

Development of Mammalian Cell Lines Which Stably Express Recombinant Human FSH Receptor or an FSH-Binding Fragment or Mutant Thereof Suitable mammalian cell lines for expression of recombinant human FSH and its derivatives include Chinese Hamster Ovary (CHO), mouse adenocarcinoma Y1, rat pituitary $GH_3$, human breast carcinoma MCF7, and human embryonic kidney 293. In this example, the use of Y1 and CHO cells is described.

Y1 cells are a clonal steroid secreting cell strain initiated from a mouse adrenal cortex tumor (Yasumura, Cancer Res. 26: 529–536, 1966.). These cells were obtained from the ATCC cell bank (ATCC CCL 79) and are maintained in culture by growth in Ham's F10 medium supplemented with 15% horse serum (HS), 2.5% FBS, and 1% L-glutamine (Y1 growth medium).

CHO-DUKX cells are a clonal mutant of Chinese hamster ovary cells lacking dihydrofolate reductase activity (Urlaub G. and Chasin, L.A. PNAS 77: 4216–4220, 1980). The cells were maintained in Minimum Essential Alpha Medium (MEM-α) supplemented with 10% FBS and 1% L-glutamine (CHO growth medium).

Calcium phosphate transfections.

24 hours prior to transfection, cells are plated on 100-mm dishes. CHO-DUKX cells are plated at a density of $7 \times 10^5$ cells/dish, Y1 cells are plated at a density of $1 \times 10^6$ cells/dish. 10 µg of the vector plasmid DNA such as the one depicted in FIG. 3 is added to 0.5 ml of transfection buffer. The buffer is prepared by adding 4 grams (g) NaCl, 0.185 g KCl, 0.05 g $Na_2HPo4$, 0.5 g dextrose, 2.5 g Hepes and sterile, distilled $H_2O$ to a final volume of 500 ml and adjusting the pH to 7.5. 31 µl of 2M $CaCl_2$ is added to the DNA/transfection buffer mixture and vortexed. This solution is allowed to stand at room temperature for 45 minutes (Graham, Virology 52: 456, 1973). After 45 minutes the media is removed from the cells and the DNA-$CaCl_2$-transfection buffer precipitate is layered over the cells. The cells are allowed to stand at room temperature for 20 minutes, after which 5 ml of the appropriate growth medium is added and the plates are incubated for 6 hours at 37°. After 6 hours, the cells are shocked by aspirating off the media and adding 5 ml of transfection buffer containing 15% glycerol for 3.5 minutes. The cells are rinsed twice with PBS prior to the addition of 10 ml growth medium. 48 hours post transfection the CHO-DUKX cells are subcultures at a 1:10 split ratio and selection medium is added. Y1 cells are allowed to grow for 72 hours post transfection before subculturing at a 1:5 split ratio in selection medium. Selection medium for DHFR in CHO-DUKX cells is prepared by adding MEM-α without ribonucleosides and ribonucleosides supplemented with 10% dialyzed FBS and 1% L-glutamine +0.02 µM methotrexate (MTX). Selection medium for Neo in Y1 cells consists of Y1 growth medium +80 µg/ml G418.

Determination of FSH in Vitro Bioactivity Using Y1 or CHO Cells Stably Transfected with the Human FSH Receptor.

In order to estimate the bioactivity of pharmaceutical preparations of FSH, CHO cells which stably express the human FSH receptor can be treated with FSH and assayed for increased cAMP levels as described above for COS-7 cells in example 2. Alternatively, a reporter gene such as luciferase, which may or may not be secreted by the cell, can be operatively linked to a cAMP response element, and increases in cAMP levels may be indirectly measured by a non-radioactive method, such as bioluminescence. If the DHFR gene was used for selection of transfected cells, the human FSH receptor content of the cell can be increased by exposing the cells to stepwise increases of MTX, so that the vector copy number in increased. This can be done, if necessary, to adjust the biological response to an optimal range for the assay.

Y1 cells which stably express the human FSH receptor can be treated with FSH and the culture medium assayed for increased levels of progesterone. A kit such as the Serono Diagnostics Progesterone MAIA, product number 12274, distributed by Ciba Corning, Medfield, Mass., can be used for this purpose.

Mammalian cells which express high levels of human FSH receptor or FSH-binding fragments or mutants thereof, can be used for the manufacture of large amounts of human FSH receptor protein for use in receptor radioimmunoassays.

We claim:

1. A method of reducing endogenous human follicle stimulating hormone (FSH) bioactivity in a patient, comprising administering to said patient, in an amount effective to reduce the endogenous FSH bioactivity, a polypeptide capable of binding FSH which includes a contiguous portion of the extracellular domain of the human FSH receptor, said domain having the sequence of amino acids 1-349 of SEQ ID NO:2 which portion retains substantially the same FSH-binding characteristics as the complete extracellular domain, or a polypeptide which includes a mutein of said portion which mutein retains at least 95% identity with said portion and which mutein retains substantially the same FSH-binding characteristic as said portion.

2. A method in accordance with claim 1, wherein said polypeptide is a polypeptide capable of binding FSH which includes a contiguous portion of the extracellular domain of the human FSH receptor, said domain having the sequence of amino acids 1-349 of SEQ ID NO:2 which portion retains substantially the same FSH-binding characteristics as the complete extracellular domain.

3. A method in accordance with claim 1, wherein said mutein differs from said portion only by conservative substitutions in one to ten amino acid residues, the location and nature of said substitutions being selected so as not to significantly degrade the FSH binding characteristics of said portion.

4. A method in accordance with claim 1, wherein said polypeptide includes amino acid sequence 1-349 of SEQ ID NO:2 or a mutein which retains at least 95% identity with said sequence and retains substantially the same FSH-binding characteristics as said sequence.

5. A method in accordance with claim 4, wherein said polypeptide includes amino acid sequence 1-349 of SEQ ID NO:2.

6. A method of preventing follicle growth and maturation in a female patient, comprising administering to said patient, in an amount effective to prevent follicle growth and maturation, a polypeptide capable of binding human follicle stimulating hormone (FSH) which includes a contiguous portion of the extracellular domain of the human FSH receptor, said domain having the sequence of amino acids 1-349 of SEQ ID NO:2 which portion retains substantially the same FSH-binding characteristics as the complete extracellular domain, or a polypeptide which includes a mutein of said portion which mutein retains at least 95% identity with said portion and which mutein retains substantially the same FSH-binding characteristic as said portion.

7. A method in accordance with claim 6, wherein said polypeptide is a polypeptide capable of binding FSH which includes a contiguous portion of the extracellular domain of the human FSH receptor, said domain having the sequence of amino acids 1-349 of SEQ ID NO:2 which portion retains substantially the same FSH-binding characteristics as the complete extracellular domain.

8. A method in accordance with claim 6, wherein said mutein differs from said portion only by conservative substitutions in one to ten amino acid residues, the location and nature of said substitutions being selected so as not to significantly degrade the FSH binding characteristics of said portion.

9. A method in accordance with claim 6, wherein said polypeptide includes amino acid sequence 1-349 of SEQ ID NO:2 or a mutein which retains at least 95% identity with said sequence and retains substantially the same FSH-binding characteristics as said sequence.

10. A method in accordance with claim 6, wherein said polypeptide includes amino acid sequence 1-349 of SEQ ID NO:2.

11. A method of preventing spermatogenesis in a male patient, comprising administering to said patient, in an amount effective to prevent spermatogenesis, a polypeptide capable of binding human follicle stimulating hormone (FSH) which includes a contiguous portion of the extracellular domain of the human FSH receptor, said domain having the sequence of amino acids 1-349 of SEQ ID NO:2 which portion retains substantially the same FSH-binding characteristics as the complete extracellular domain, or a polypeptide which includes a mutein of said portion which mutein retains at least 95% identity with said portion and which mutein retains substantially the same FSH-binding characteristic as said portion.

12. A method in accordance with claim 11, wherein said polypeptide is a polypeptide capable of binding FSH which includes a contiguous portion of the extracellular domain of the human FSH receptor, which portion retains substantially the same FSH-binding characteristics as the complete extracellular domain.

13. A method in accordance with claim 11, wherein said mutein differs from said portion only by conservative substitutions in one to ten amino acid residues, the location and nature of said substitutions being selected so as not to significantly degrade the FSH binding characteristics of said portion.

14. A method in accordance with claim 11, wherein said polypeptide includes amino acid sequence 1-349 of SEQ ID NO:2 or a mutein which retains at least 95% identity with said sequence and retains substantially the same FSH-binding characteristics as said sequence.

15. A method in accordance with claim 11, wherein said polypeptide includes amino acid sequence 1-349 of SEQ ID NO:2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2179
        ( B ) TYPE: Nucleic acid
        ( C ) STRANDEDNESS: Double
        ( D ) TOPOLOGY: Linear ( i i ) MOLECULE TYPE: cDNA to mRNA ( v i ) ORIGINAL SOURCE:
        ( A ) ORGANISM: Homo sapiens
        ( F ) TISSUE TYPE: Testis ( v i i ) IMMEDIATE SOURCE:
        ( A ) LIBRARY: lgt11 cDNA library, ClonTech #HL1010b
        ( B ) CLONE: pHFSHR11-11, pHFSHR15- 6

( i x ) FEATURE:
        ( A ) NAME/KEY: protein coding region
        ( B ) LOCATION: 75 to 2159

( x i ) SEQUENCE DESCRIPTION: SEQ ID NO:1:

```
TGTGGAGCTT  CTGAGATCTG  TGGAGGTTTT  TCTCTGCAAA  TGCAGGAAGA  AATCAGGTGG        60

ATGGATGCAT  AATT ATG GCC CTG CTC CTG GTC TCT TTG CTG GCA TTC CTG             110
              Met Ala Leu Leu Leu Val Ser Leu Leu Ala Phe Leu
                  -15                         -10

AGC TTG GGC TCA GGA TGT CAT CAT CGG ATC TGT CAC TGC TCT AAC AGG              158
Ser Leu Gly Ser Gly Cys His His Arg Ile Cys His Cys Ser Asn Arg
 -5              1               5               10

GTT TTT CTC TGC CAA GAG AGC AAG GTG ACA GAG ATT CCT TCT GAC CTC              206
Val Phe Leu Cys Gln Glu Ser Lys Val Thr Glu Ile Pro Ser Asp Leu
             15              20              25

CCG AGG AAT GCC ATT GAA CTG AGG TTT GTC CTC ACC AAG CTT CGA GTC              254
Pro Arg Asn Ala Ile Glu Leu Arg Phe Val Leu Thr Lys Leu Arg Val
         30              35              40

ATC CAA AAA GGT GCA TTT TCA GGA TTT GGG GAC CTG GAG AAA ATA GAG              302
Ile Gln Lys Gly Ala Phe Ser Gly Phe Gly Asp Leu Glu Lys Ile Glu
     45              50              55

ATC TCT CAG AAT GAT GTC TTG GAG GTG ATA GAG GCA GAT GTG TTC TCC              350
Ile Ser Gln Asn Asp Val Leu Glu Val Ile Glu Ala Asp Val Phe Ser
 60              65              70              75

AAC CTT CCC AAA TTA CAT GAA ATT AGA ATT GAA AAG GCC AAC AAC CTG              398
Asn Leu Pro Lys Leu His Glu Ile Arg Ile Glu Lys Ala Asn Asn Leu
             80              85              90

CTC TAC ATC AAC CCT GAG GCC TTC CAG AAC CTT CCC AAC CTT CAA TAT              446
Leu Tyr Ile Asn Pro Glu Ala Phe Gln Asn Leu Pro Asn Leu Gln Tyr
         95              100             105

CTG TTA ATA TCC AAC ACA GGT ATT AAG CAC CTT CCA GAT GTT CAC AAG              494
Leu Leu Ile Ser Asn Thr Gly Ile Lys His Leu Pro Asp Val His Lys
```

-continued

|     |     |     | 110 |     |     |     |     | 115 |     |     |     |     | 120 |     |     |      |
|-----|-----|-----|-----|-----|-----|-----|-----|-----|-----|-----|-----|-----|-----|-----|-----|------|
| ATT | CAT | TCT | CTC | CAA | AAA | GTT | TTA | CTT | GAC | ATT | CAA | GAT | AAC | ATA | AAC | 542  |
| Ile | His | Ser | Leu | Gln | Lys | Val | Leu | Leu | Asp | Ile | Gln | Asp | Asn | Ile | Asn |      |
|     | 125 |     |     |     |     | 130 |     |     |     |     | 135 |     |     |     |     |      |

| ATC | CAC | ACA | ATT | GAA | AGA | AAT | TCT | TTC | GTG | GGG | CTG | AGC | TTT | GAA | AGT | 590  |
| Ile | His | Thr | Ile | Glu | Arg | Asn | Ser | Phe | Val | Gly | Leu | Ser | Phe | Glu | Ser |      |
| 140 |     |     |     |     | 145 |     |     |     |     | 150 |     |     |     |     | 155 |      |

| GTG | ATT | CTA | TGG | CTG | AAT | AAG | AAT | GGG | ATT | CAA | GAA | ATA | CAC | AAC | TGT | 638  |
| Val | Ile | Leu | Trp | Leu | Asn | Lys | Asn | Gly | Ile | Gln | Glu | Ile | His | Asn | Cys |      |
|     |     |     |     |     | 160 |     |     |     |     | 165 |     |     |     | 170 |     |      |

| GCA | TTC | AAT | GGA | ACC | CAA | CTA | GAT | GAG | CTG | AAT | CTA | AGC | GAT | AAT | AAT | 686  |
| Ala | Phe | Asn | Gly | Thr | Gln | Leu | Asp | Glu | Leu | Asn | Leu | Ser | Asp | Asn | Asn |      |
|     |     |     |     | 175 |     |     |     | 180 |     |     |     |     | 185 |     |     |      |

| AAT | TTA | GAA | GAA | TTG | CCT | AAT | GAT | GTT | TTC | CAC | GGA | GCC | TCT | GGA | CCA | 734  |
| Asn | Leu | Glu | Glu | Leu | Pro | Asn | Asp | Val | Phe | His | Gly | Ala | Ser | Gly | Pro |      |
|     |     | 190 |     |     |     |     | 195 |     |     |     |     | 200 |     |     |     |      |

| GTC | ATT | CTA | GAT | ATT | TCA | AGA | ACA | AGG | ATC | CAT | TCC | CTG | CCT | AGC | TAT | 782  |
| Val | Ile | Leu | Asp | Ile | Ser | Arg | Thr | Arg | Ile | His | Ser | Leu | Pro | Ser | Tyr |      |
|     | 205 |     |     |     |     | 210 |     |     |     |     | 215 |     |     |     |     |      |

| GGC | TTA | GAA | AAT | CTT | AAG | AAG | CTG | AGG | GCC | AGG | TCG | ACT | TAC | AAC | TTA | 830  |
| Gly | Leu | Glu | Asn | Leu | Lys | Lys | Leu | Arg | Ala | Arg | Ser | Thr | Tyr | Asn | Leu |      |
| 220 |     |     |     |     | 225 |     |     |     |     | 230 |     |     |     |     | 235 |      |

| AAA | AAG | CTG | CCT | ACT | CTG | GAA | AAG | CTT | GTC | GCC | CTC | ATG | GAA | GCC | AGC | 878  |
| Lys | Lys | Leu | Pro | Thr | Leu | Glu | Lys | Leu | Val | Ala | Leu | Met | Glu | Ala | Ser |      |
|     |     |     |     | 240 |     |     |     |     | 245 |     |     |     |     | 250 |     |      |

| CTC | ACC | TAT | CCC | AGC | CAT | TGC | TGT | GCC | TTT | GCA | AAC | TGG | AGA | CGG | CAA | 926  |
| Leu | Thr | Tyr | Pro | Ser | His | Cys | Cys | Ala | Phe | Ala | Asn | Trp | Arg | Arg | Gln |      |
|     |     |     | 255 |     |     |     |     | 260 |     |     |     |     | 265 |     |     |      |

| ATC | TCT | GAG | CTT | CAT | CCA | ATT | TGC | AAC | AAA | TCT | ATT | TTA | AGG | CAA | GAA | 974  |
| Ile | Ser | Glu | Leu | His | Pro | Ile | Cys | Asn | Lys | Ser | Ile | Leu | Arg | Gln | Glu |      |
|     |     | 270 |     |     |     |     | 275 |     |     |     |     | 280 |     |     |     |      |

| GTT | GAT | TAT | ATG | ACT | CAG | ACT | AGG | GGT | CAG | AGA | TCC | TCT | CTG | GCA | GAA | 1022 |
| Val | Asp | Tyr | Met | Thr | Gln | Thr | Arg | Gly | Gln | Arg | Ser | Ser | Leu | Ala | Glu |      |
|     | 285 |     |     |     |     | 290 |     |     |     |     | 295 |     |     |     |     |      |

| GAC | AAT | GAG | TCC | AGC | TAC | AGC | AGA | GGA | TTT | GAC | ATG | ACG | TAC | ACT | GAG | 1070 |
| Asp | Asn | Glu | Ser | Ser | Tyr | Ser | Arg | Gly | Phe | Asp | Met | Thr | Tyr | Thr | Glu |      |
| 300 |     |     |     |     | 305 |     |     |     |     | 310 |     |     |     |     | 315 |      |

| TTT | GAC | TAT | GAC | TTA | TGC | AAT | GAA | GTG | GTT | GAC | GTG | ACC | TGC | TCC | CCT | 1118 |
| Phe | Asp | Tyr | Asp | Leu | Cys | Asn | Glu | Val | Val | Asp | Val | Thr | Cys | Ser | Pro |      |
|     |     |     |     | 320 |     |     |     |     | 325 |     |     |     |     | 330 |     |      |

| AAG | CCA | GAT | GCA | TTC | AAC | CCA | TGT | GAA | GAT | ATC | ATG | GGG | TAC | AAC | ATC | 1166 |
| Lys | Pro | Asp | Ala | Phe | Asn | Pro | Cys | Glu | Asp | Ile | Met | Gly | Tyr | Asn | Ile |      |
|     |     |     | 335 |     |     |     |     | 340 |     |     |     |     | 345 |     |     |      |

| CTC | AGA | GTC | CTG | ATA | TGG | TTT | ATC | AGC | ATC | CTG | GCC | ATC | ACT | GGG | AAC | 1214 |
| Leu | Arg | Val | Leu | Ile | Trp | Phe | Ile | Ser | Ile | Leu | Ala | Ile | Thr | Gly | Asn |      |
|     |     |     | 350 |     |     |     |     | 355 |     |     |     |     | 360 |     |     |      |

| ATC | ATA | GTG | CTA | GTG | ATC | CTA | ACT | ACC | AGC | CAA | TAT | AAA | CTC | ACA | GTC | 1262 |
| Ile | Ile | Val | Leu | Val | Ile | Leu | Thr | Thr | Ser | Gln | Tyr | Lys | Leu | Thr | Val |      |
|     | 365 |     |     |     |     | 370 |     |     |     |     | 375 |     |     |     |     |      |

| CCC | AGG | TTC | CTT | ATG | TGC | AAC | CTG | GCC | TTT | GCT | GAT | CTC | TGC | ATT | GGA | 1310 |
| Pro | Arg | Phe | Leu | Met | Cys | Asn | Leu | Ala | Phe | Ala | Asp | Leu | Cys | Ile | Gly |      |
| 380 |     |     |     |     | 385 |     |     |     |     | 390 |     |     |     |     | 395 |      |

| ATC | TAC | CTG | CTG | CTC | ATT | GCA | TCA | GTT | GAT | ATC | CAT | ACC | AAG | AGC | CAA | 1358 |
| Ile | Tyr | Leu | Leu | Leu | Ile | Ala | Ser | Val | Asp | Ile | His | Thr | Lys | Ser | Gln |      |
|     |     |     |     | 400 |     |     |     |     | 405 |     |     |     |     | 410 |     |      |

| TAT | CAC | AAC | TAT | GCC | ATT | GAC | TGG | CAA | ACT | GGG | GCA | GGC | TGT | GAT | GCT | 1406 |
| Tyr | His | Asn | Tyr | Ala | Ile | Asp | Trp | Gln | Thr | Gly | Ala | Gly | Cys | Asp | Ala |      |
|     |     |     | 415 |     |     |     |     | 420 |     |     |     |     | 425 |     |     |      |

| GCT | GGC | TTT | TTC | ACT | GTC | TTT | GCC | AGT | GAG | CTG | TCA | GTC | TAC | ACT | CTG | 1454 |
| Ala | Gly | Phe | Phe | Thr | Val | Phe | Ala | Ser | Glu | Leu | Ser | Val | Tyr | Thr | Leu |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 430 |     |     |     |     | 435 |     |     |     |     | 440 |     |     |      |
| ACA | GCT | ATC | ACC | TTG | GAA | AGA | TGG | CAT | ACC | ATC | ACG | CAT | GCC | ATG | CAG | 1502 |
| Thr | Ala | Ile | Thr | Leu | Glu | Arg | Trp | His | Thr | Ile | Thr | His | Ala | Met | Gln |      |
|     |     | 445 |     |     |     |     | 450 |     |     |     |     | 455 |     |     |     |      |
| CTG | GAC | TGC | AAG | GTG | CAG | CTC | CGC | CAT | GCT | GCC | AGT | GTC | ATG | GTG | ATG | 1550 |
| Leu | Asp | Cys | Lys | Val | Gln | Leu | Arg | His | Ala | Ala | Ser | Val | Met | Val | Met |      |
| 460 |     |     |     |     | 465 |     |     |     |     | 470 |     |     |     |     | 475 |      |
| GGC | TGG | ATT | TTT | GCT | TTT | GCA | GCT | GCC | CTC | TTT | CCC | ATC | TTT | GGC | ATC | 1598 |
| Gly | Trp | Ile | Phe | Ala | Phe | Ala | Ala | Ala | Leu | Phe | Pro | Ile | Phe | Gly | Ile |      |
|     |     |     |     | 480 |     |     |     |     | 485 |     |     |     |     | 490 |     |      |
| AGC | AGC | TAC | ATG | AAG | GTG | AGC | ATC | TGC | CTG | CCC | ATG | GAT | ATT | GAC | AGC | 1646 |
| Ser | Ser | Tyr | Met | Lys | Val | Ser | Ile | Cys | Leu | Pro | Met | Asp | Ile | Asp | Ser |      |
|     |     |     | 495 |     |     |     |     | 500 |     |     |     |     | 505 |     |     |      |
| CCT | TTG | TCA | CAG | CTG | TAT | GTC | ATG | TCC | CTC | CTT | GTG | CTC | AAT | GTC | CTG | 1694 |
| Pro | Leu | Ser | Gln | Leu | Tyr | Val | Met | Ser | Leu | Leu | Val | Leu | Asn | Val | Leu |      |
|     |     | 510 |     |     |     |     | 515 |     |     |     |     | 520 |     |     |     |      |
| GCC | TTT | GTG | GTC | ATC | TGT | GGC | TGC | TAT | ATC | CAC | ATC | TAC | CTC | ACA | GTG | 1742 |
| Ala | Phe | Val | Val | Ile | Cys | Gly | Cys | Tyr | Ile | His | Ile | Tyr | Leu | Thr | Val |      |
|     | 525 |     |     |     |     | 530 |     |     |     |     | 535 |     |     |     |     |      |
| CGG | AAC | CCC | AAC | ATC | GTG | TCC | TCC | TCT | AGT | GAC | ACC | AGG | ATC | GCC | AAG | 1790 |
| Arg | Asn | Pro | Asn | Ile | Val | Ser | Ser | Ser | Ser | Asp | Thr | Arg | Ile | Ala | Lys |      |
| 540 |     |     |     |     | 545 |     |     |     |     | 550 |     |     |     |     | 555 |      |
| CGC | ATG | GCC | ATG | CTC | ATC | TTC | ACT | GAC | TTC | CTC | TGC | ATG | GCA | CCC | ATT | 1838 |
| Arg | Met | Ala | Met | Leu | Ile | Phe | Thr | Asp | Phe | Leu | Cys | Met | Ala | Pro | Ile |      |
|     |     |     |     | 560 |     |     |     |     | 565 |     |     |     |     | 570 |     |      |
| TCT | TTC | TTT | GCC | ATT | TCT | GCC | TCC | CTC | AAG | GTG | CCC | CTC | ATC | ACT | GTG | 1886 |
| Ser | Phe | Phe | Ala | Ile | Ser | Ala | Ser | Leu | Lys | Val | Pro | Leu | Ile | Thr | Val |      |
|     |     |     | 575 |     |     |     |     | 580 |     |     |     |     | 585 |     |     |      |
| TCC | AAA | GCA | AAG | ATT | CTG | CTG | GTT | CTG | TTT | CAC | CCC | ATC | AAC | TCC | TGT | 1934 |
| Ser | Lys | Ala | Lys | Ile | Leu | Leu | Val | Leu | Phe | His | Pro | Ile | Asn | Ser | Cys |      |
|     |     | 590 |     |     |     |     | 595 |     |     |     |     | 600 |     |     |     |      |
| GCC | AAC | CCC | TTC | CTC | TAT | GCC | ATC | TTT | ACC | AAA | AAC | TTT | CGC | AGA | GAT | 1982 |
| Ala | Asn | Pro | Phe | Leu | Tyr | Ala | Ile | Phe | Thr | Lys | Asn | Phe | Arg | Arg | Asp |      |
|     | 605 |     |     |     |     | 610 |     |     |     |     | 615 |     |     |     |     |      |
| TTC | TTC | ATT | CTG | CTG | AGC | AAG | TGT | GGC | TGC | TAT | GAA | ATG | CAA | GCC | CAA | 2030 |
| Phe | Phe | Ile | Leu | Leu | Ser | Lys | Cys | Gly | Cys | Tyr | Glu | Met | Gln | Ala | Gln |      |
| 620 |     |     |     |     | 625 |     |     |     |     | 630 |     |     |     |     | 635 |      |
| ATT | TAT | AGG | ACA | GAA | ACT | TCA | TCC | ACT | GTC | CAC | AAC | ACC | CAT | CCA | AGG | 2078 |
| Ile | Tyr | Arg | Thr | Glu | Thr | Ser | Ser | Thr | Val | His | Asn | Thr | His | Pro | Arg |      |
|     |     |     |     | 640 |     |     |     |     | 645 |     |     |     |     | 650 |     |      |
| AAT | GGC | CAC | TGC | TCT | TCA | GCT | CCC | AGA | GTC | ACC | AAT | GGT | TCC | ACT | TAC | 2126 |
| Asn | Gly | His | Cys | Ser | Ser | Ala | Pro | Arg | Val | Thr | Asn | Gly | Ser | Thr | Tyr |      |
|     |     |     | 655 |     |     |     |     | 660 |     |     |     |     | 665 |     |     |      |
| ATA | CTT | GTC | CCT | CTA | AGT | CAT | TTA | GCC | CAA | AAC | TAAAACACAA | | TGTGAAAATG | | | 2179 |
| Ile | Leu | Val | Pro | Leu | Ser | His | Leu | Ala | Gln | Asn |     |     |     |     |     |      |
|     |     | 670 |     |     |     |     | 675 |     |     |     |     |     |     |     |     |      |

(2) INFORMATION FOR SEQ ID NO:2:

(i) SEQUENCE CHARACTERISTICS:
        (A) LENGTH: 695
        (B) TYPE: Amino acid
        (D) TOPOLOGY: Linear (ii) MOLECULE TYPE: protein (ix) FEATURE:
        (A) NAME/KEY: signal sequence
        (B) LOCATION: -17 to -1
        (C) IDENTIFICATION METHOD: hydrophobic (ix) FEATURE:
        (A) NAME/KEY: putative amino- terminal extracellular domain
        (B) LOCATION: 1 to 349

( C ) IDENTIFICATION METHOD: similarity with other
dimeric glycoprotein receptor extracellular
domains, hydrophilic ( i x ) FEATURE:
( A ) NAME/KEY: transmembrane domain
( B ) LOCATION: 350 to 613
( C ) IDENTIFICATION METHOD: similarity to other G
protein- coupled receptor transmembrane domains ( i x ) FEATURE:
( A ) NAME/KEY: putative transmembrane region I
( B ) LOCATION: 350 to 370
( C ) IDENTIFICATION METHOD: similarity to other G
protein- coupled receptor transmembrane regions,
hydrophobic, about 20-23 amino acids in length ( i x ) FEATURE:
( A ) NAME/KEY: putative transmembrane region II
( B ) LOCATION: 382 to 404
( C ) IDENTIFICATION METHOD: similarity to other G
protein- coupled receptor transmembrane regions,
hydrophobic, about 20-23 amino acids in length ( i x ) FEATURE:
( A ) NAME/KEY: putative transmembrane region III
( B ) LOCATION: 427 to 448
( C ) IDENTIFICATION METHOD: similarity to other G
protein- coupled receptor transmembrane regions,
hydrophobic, about 20-23 amino acids in length ( i x ) FEATURE:
( A ) NAME/KEY: putative transmembrane region IV
( B ) LOCATION: 469 to 491
( C ) IDENTIFICATION METHOD: similarity to other G
protein- coupled receptor transmembrane regions,
hydrophobic, about 20-23 amino acids in length ( i x ) FEATURE:
( A ) NAME/KEY: putative transmembrane region V
( B ) LOCATION: 512 to 533
( C ) IDENTIFICATION METHOD: similarity to other G
protein- coupled receptor transmembrane regions,
hydrophobic, about 20-23 amino acids in length ( i x ) FEATURE:
( A ) NAME/KEY: putative transmembrane region VI
( B ) LOCATION: 557 to 580
( C ) IDENTIFICATION METHOD: similarity to other G
protein- coupled receptor transmembrane regions,
hydrophobic, about 20-23 amino acids in length ( i x ) FEATURE:
( A ) NAME/KEY: putative transmembrane region VII
( B ) LOCATION: 592 to 613
( C ) IDENTIFICATION METHOD: similarity to other G
protein- coupled receptor transmembrane regions,
hydrophobic, about 20-23 amino acids in length ( i x ) FEATURE:
( A ) NAME/KEY: putative carboxy- terminal intracellular
domain
( B ) LOCATION: 614 to 678

( x i ) SEQUENCE DESCRIPTION: SEQ ID NO:2:

```
Met Ala Leu Leu Leu Val Ser Leu Leu Ala Phe Leu Ser Leu Gly Ser
        -15                 -10                  -5

Gly Cys His His Arg Ile Cys His Cys Ser Asn Arg Val Phe Leu Cys
     1            5                  10                      15

Gln Glu Ser Lys Val Thr Glu Ile Pro Ser Asp Leu Pro Arg Asn Ala
                  20                  25                  30

Ile Glu Leu Arg Phe Val Leu Thr Lys Leu Arg Val Ile Gln Lys Gly
             35                  40                  45

Ala Phe Ser Gly Phe Gly Asp Leu Glu Lys Ile Glu Ile Ser Gln Asn
         50                  55                  60
```

| | | | | | | | | | | | | | | |
|---|---|---|---|---|---|---|---|---|---|---|---|---|---|---|
| Asp | Val | Leu | Glu | Val | Ile | Glu | Ala | Asp | Val | Phe | Ser | Asn | Leu | Pro | Lys |
| | | 65 | | | | 70 | | | | 75 | | | | | |
| Leu | His | Glu | Ile | Arg | Ile | Glu | Lys | Ala | Asn | Asn | Leu | Leu | Tyr | Ile | Asn |
| 80 | | | | | 85 | | | | | 90 | | | | | 95 |
| Pro | Glu | Ala | Phe | Gln | Asn | Leu | Pro | Asn | Leu | Gln | Tyr | Leu | Leu | Ile | Ser |
| | | | | 100 | | | | | 105 | | | | | 110 | |
| Asn | Thr | Gly | Ile | Lys | His | Leu | Pro | Asp | Val | His | Lys | Ile | His | Ser | Leu |
| | | | 115 | | | | | 120 | | | | | 125 | | |
| Gln | Lys | Val | Leu | Leu | Asp | Ile | Gln | Asp | Asn | Ile | Asn | Ile | His | Thr | Ile |
| | | 130 | | | | | 135 | | | | | 140 | | | |
| Glu | Arg | Asn | Ser | Phe | Val | Gly | Leu | Ser | Phe | Glu | Ser | Val | Ile | Leu | Trp |
| | 145 | | | | | 150 | | | | | 155 | | | | |
| Leu | Asn | Lys | Asn | Gly | Ile | Gln | Glu | Ile | His | Asn | Cys | Ala | Phe | Asn | Gly |
| 160 | | | | | 165 | | | | | 170 | | | | | 175 |
| Thr | Gln | Leu | Asp | Glu | Leu | Asn | Leu | Ser | Asp | Asn | Asn | Asn | Leu | Glu | Glu |
| | | | | 180 | | | | | 185 | | | | | 190 | |
| Leu | Pro | Asn | Asp | Val | Phe | His | Gly | Ala | Ser | Gly | Pro | Val | Ile | Leu | Asp |
| | | | 195 | | | | | 200 | | | | | 205 | | |
| Ile | Ser | Arg | Thr | Arg | Ile | His | Ser | Leu | Pro | Ser | Tyr | Gly | Leu | Glu | Asn |
| | | 210 | | | | | 215 | | | | | 220 | | | |
| Leu | Lys | Lys | Leu | Arg | Ala | Arg | Ser | Thr | Tyr | Asn | Leu | Lys | Lys | Leu | Pro |
| | 225 | | | | | 230 | | | | | 235 | | | | |
| Thr | Leu | Glu | Lys | Leu | Val | Ala | Leu | Met | Glu | Ala | Ser | Leu | Thr | Tyr | Pro |
| 240 | | | | | 245 | | | | | 250 | | | | | 255 |
| Ser | His | Cys | Cys | Ala | Phe | Ala | Asn | Trp | Arg | Arg | Gln | Ile | Ser | Glu | Leu |
| | | | 260 | | | | | 265 | | | | | 270 | | |
| His | Pro | Ile | Cys | Asn | Lys | Ser | Ile | Leu | Arg | Gln | Glu | Val | Asp | Tyr | Met |
| | | | 275 | | | | | 280 | | | | | 285 | | |
| Thr | Gln | Thr | Arg | Gly | Gln | Arg | Ser | Ser | Leu | Ala | Glu | Asp | Asn | Glu | Ser |
| | | | 290 | | | | 295 | | | | | 300 | | | |
| Ser | Tyr | Ser | Arg | Gly | Phe | Asp | Met | Thr | Tyr | Thr | Glu | Phe | Asp | Tyr | Asp |
| | 305 | | | | | 310 | | | | | 315 | | | | |
| Leu | Cys | Asn | Glu | Val | Val | Asp | Val | Thr | Cys | Ser | Pro | Lys | Pro | Asp | Ala |
| 320 | | | | | 325 | | | | | 330 | | | | | 335 |
| Phe | Asn | Pro | Cys | Glu | Asp | Ile | Met | Gly | Tyr | Asn | Ile | Leu | Arg | Val | Leu |
| | | | | 340 | | | | | 345 | | | | | 350 | |
| Ile | Trp | Phe | Ile | Ser | Ile | Leu | Ala | Ile | Thr | Gly | Asn | Ile | Ile | Val | Leu |
| | | | 355 | | | | | 360 | | | | | 365 | | |
| Val | Ile | Leu | Thr | Thr | Ser | Gln | Tyr | Lys | Leu | Thr | Val | Pro | Arg | Phe | Leu |
| | | | 370 | | | | | 375 | | | | | 380 | | |
| Met | Cys | Asn | Leu | Ala | Phe | Ala | Asp | Leu | Cys | Ile | Gly | Ile | Tyr | Leu | Leu |
| | 385 | | | | | 390 | | | | | 395 | | | | |
| Leu | Ile | Ala | Ser | Val | Asp | Ile | His | Thr | Lys | Ser | Gln | Tyr | His | Asn | Tyr |
| 400 | | | | | 405 | | | | | 410 | | | | | 415 |
| Ala | Ile | Asp | Trp | Gln | Thr | Gly | Ala | Gly | Cys | Asp | Ala | Ala | Gly | Phe | Phe |
| | | | | 420 | | | | | 425 | | | | | 430 | |
| Thr | Val | Phe | Ala | Ser | Glu | Leu | Ser | Val | Tyr | Thr | Leu | Thr | Ala | Ile | Thr |
| | | | 435 | | | | | 440 | | | | | 445 | | |
| Leu | Glu | Arg | Trp | His | Thr | Ile | Thr | His | Ala | Met | Gln | Leu | Asp | Cys | Lys |
| | | | 450 | | | | | 455 | | | | | 460 | | |
| Val | Gln | Leu | Arg | His | Ala | Ala | Ser | Val | Met | Val | Met | Gly | Trp | Ile | Phe |
| | 465 | | | | | 470 | | | | | 475 | | | | |
| Ala | Phe | Ala | Ala | Ala | Leu | Phe | Pro | Ile | Phe | Gly | Ile | Ser | Ser | Tyr | Met |

-continued

| 480 | | | | | 485 | | | | 490 | | | | 495 | |
|---|---|---|---|---|---|---|---|---|---|---|---|---|---|---|
| Lys | Val | Ser | Ile | Cys 500 | Leu | Pro | Met | Asp | Ile 505 | Asp | Ser | Pro | Leu | Ser 510 | Gln |
| Leu | Tyr | Val | Met 515 | Ser | Leu | Leu | Val | Leu 520 | Asn | Val | Leu | Ala | Phe 525 | Val | Val |
| Ile | Cys | Gly 530 | Cys | Tyr | Ile | His | Ile 535 | Tyr | Leu | Thr | Val | Arg 540 | Asn | Pro | Asn |
| Ile | Val 545 | Ser | Ser | Ser | Ser | Asp 550 | Thr | Arg | Ile | Ala | Lys 555 | Arg | Met | Ala | Met |
| Leu 560 | Ile | Phe | Thr | Asp | Phe 565 | Leu | Cys | Met | Ala | Pro 570 | Ile | Ser | Phe | Phe | Ala 575 |
| Ile | Ser | Ala | Ser | Leu 580 | Lys | Val | Pro | Leu | Ile 585 | Thr | Val | Ser | Lys | Ala 590 | Lys |
| Ile | Leu | Leu | Val 595 | Leu | Phe | His | Pro | Ile 600 | Asn | Ser | Cys | Ala | Asn 605 | Pro | Phe |
| Leu | Tyr | Ala 610 | Ile | Phe | Thr | Lys | Asn 615 | Phe | Arg | Arg | Asp | Phe 620 | Phe | Ile | Leu |
| Leu | Ser 625 | Lys | Cys | Gly | Cys | Tyr 630 | Glu | Met | Gln | Ala | Gln 635 | Ile | Tyr | Arg | Thr |
| Glu 640 | Thr | Ser | Ser | Thr | Val 645 | His | Asn | Thr | His | Pro 650 | Arg | Asn | Gly | His | Cys 655 |
| Ser | Ser | Ala | Pro | Arg 660 | Val | Thr | Asn | Gly | Ser 665 | Thr | Tyr | Ile | Leu | Val 670 | Pro |
| Leu | Ser | His | Leu 675 | Ala | Gln | Asn | | | | | | | | | |